United States Patent [19]

Miura et al.

[11] Patent Number: 5,116,828

[45] Date of Patent: May 26, 1992

[54] PHARMACEUTICAL COMPOSITION FOR TREATMENT OF OSTEOPOROSIS

[75] Inventors: Tomoshi Miura; Shinichiro Aonuma; Hiroyuki Ohara, all of Hyogo, Japan

[73] Assignee: Nippon Zoki Pharmaceutical Co., Ltd., Osaka, Japan

[21] Appl. No.: 603,214

[22] Filed: Oct. 25, 1990

[30] Foreign Application Priority Data

Oct. 26, 1989 [JP] Japan ................................. 1-281141

[51] Int. Cl.$^5$ .................... A61K 31/565; A61K 37/24
[52] U.S. Cl. ................................................. 514/171
[58] Field of Search ......................................... 514/171

[56] References Cited

U.S. PATENT DOCUMENTS

| | | | |
|---|---|---|---|
| 4,041,022 | 8/1977 | Neher et al. | 514/177 |
| 4,590,184 | 5/1986 | Maeda et al. | 514/167 |
| 4,692,433 | 9/1987 | Hostetler et al. | 514/805 |
| 4,812,304 | 3/1989 | Anderson et al. | 514/167 |
| 4,812,311 | 3/1989 | Vchtman | 514/167 |
| 4,822,609 | 4/1989 | Flora | 514/167 |
| 4,945,103 | 7/1990 | Cohen | 514/167 |
| 4,946,679 | 8/1990 | Thys-Jacobs | 514/899 |
| 5,001,118 | 3/1991 | Maeda et al. | 514/167 |

FOREIGN PATENT DOCUMENTS 63-290828A 11/1988 Japan .
2138286A 10/1984 United Kingdom .

OTHER PUBLICATIONS

Glass Derwent Abstract 66-36744f/00 of FR.6435m, Bel 6.877713-A "Topical Compn of Sodium L-Thyroxine and an Estrogen: Synthetic or Natural eg. Stilbesterol, Diethylstilbestorol, Mestranol, Estrone, B-Estradiol, Ethinyl Estradoil, and Vitamin A".
Woodard Chem. Abstr. 74:50183k (1971).
Maeda Chem. Abstr. 77:56947w (1972).

Primary Examiner—Shep K. Rose
Attorney, Agent, or Firm—Oliff & Berridge

[57] ABSTRACT

A pharmaceutical composition for the treatment of osteoporosis comprises an estrogen and a thyroid hormone as effective ingredients. By using the estrogen in combination with the thyroid hormone, a more excellent activity of increasing bone amount can be obtained than in the case of administering the estrogen alone.

8 Claims, No Drawings

PHARMACEUTICAL COMPOSITION FOR TREATMENT OF OSTEOPOROSIS

BACKGROUND OF THE INVENTION

The present invention relates to pharmaceutical compositions for the treatment of osteoporosis comprising an estrogen and a thyroid hormone as effective ingredients.

Osteoporosis is a disease which has been most notably observed among senile bone diseases and refers degenerative change by aging. In osteoporosis, a small impact leads to compression fracture of the spinal cord or bone fractures of the legs and arms, which cause pain or functional disorder.

As causes for osteoporosis, endocrine factors nutritional factors, physical factors, genetic factors, etc. have been considered; inter alia, osteoporosis sharply increases in postmenopausal women occurs at an early stage in women who underwent oophorectomy. From these facts, it is suggested that there might be a serious relationship between the incidence of osteoporosis and decrease in sex hormone, especially an estrogen, accompanied by menopause.

That is, it is known that due to the lack of an estrogen which rapidly proceeds after menopause, absorption of calcium is inhibited and at the same time, reduced synthesis of vitamin D is caused. It is thus considered that deficiency of the estrogen would be one of the important causes for osteoporosis. In recent years, an estrogen receptor was found in osteoblast so that a basis for direct action of the estrogen on bones is being clarified. In fact, the estrogen has been used in American and European countries as a first choice drug for the treatment of osteoporosis.

However, the estrogen causes unpleasant side effects such as uterine bleeding, mastoncus, etc. and might also induce endometrial cancer of breast cancer. Therefore, it is the actual situation in Japan that the estrogen has not been used very often.

During the course of investigations on safe drugs having a high therapeutic effect on osteoporosis, the present inventors have found that pharmaceutical compositions comprising an estrogen in combination with a thyroid hormone exhibit a superior therapeutic effect to the case of administering the estrogen alone. The present invention has thus been accomplished.

SUMMARY OF THE INVENTION

An object of the present inventions to provide pharmaceutical compositions for the treatment of osteoporosis comprising an estrogen and a thyroid hormone as effective ingredients.

DETAILED DESCRIPTION OF PREFERRED EMBODIMENTS

The estrogen in the pharmaceutical composition of the present invention includes an estrogen which is actually used for the treatment of osteoporosis in estrogen replacement therapy and an estrogen which is suggested to have a therapeutic effect on osteoporosis in clinical tests or animal tests, etc. More specifically, natural estrogens, natural estrogen precursors and derivatives thereof may be used. Examples of such estrogens include natural estrogens such as estrone, estradiol, estriol, etc.; natural estrogen precursors such as $\Delta^4$-androstenedione, $\Delta^5$-androstenediol, testosterone, dehydroepiandrosterone, pregnenolone, 17α-OH-Pregnenolone, progesterone, 17α-OH-progesterone, 17α-20α-OH-progesterone, etc.; derivatives of natural estrogens and natural estrogen precursors such as ethynylestradiol, mestranol, estrone sulfate sodium salt, equilin sulfate sodium salt, prasterone sulfate sodium salt, etc.

In the present invention, the estrogen also includes esters of the aforesaid estrogens and pharmaceutically acceptable salts thereof. Examples of the esters include esters with formic acid, acetic acid, propionic acid, butyric acid, isobutyric acid, valeric acid, caproic acid, enanthic acid, glycolic acid, citric acid, tartaric acid, succinic acid, gluconic acid, lactic acid, malonic acid, fumaric acid, benzoic acid, anthranilic acid, cinnamic acid, etc.; and examples of the salts include salts with alkali metals such as sodium, potassium, etc. and alkaline earth metals such as calcium, etc. As drugs, there may be used esters, for example, estradiol propionate, estradiol valerate, estradiol benzoate, estriol propionate, estriol benzoate, testosterone propionate, testosterone enanthate, etc.

As the thyroid hormone which is another effective ingredient in the pharmaceutical composition of the present invention, L-thyroxine, L-triiodothyronine and pharmaceutically acceptable salts thereof with sodium, etc. can be used.

The pharmaceutical composition of the present invention can be prepared using each one of the estrogen and thyroid hormones described above or using several kinds thereof in combination.

Desired doses of the estrogen and the thyroid hormone, which are the effective ingredients in the composition of the present invention for the treatment of osteoporosis, may be suitably varied depending on kind of the estrogen and thyroid hormone, subject to be administered, preparation form, route for administration, period for administration, etc. In order to obtain desired therapeutic effects, however, examples of preferred doses for adult are shown below. In producing medical preparations, the estrogen and the thyroid hormone are appropriately formulated so as to meet the respective doses in the pharmaceutical composition.

I. Estrogen (1) Estradiol benzoate
   0.1–5 mg/day (subcutaneous, intramuscular)
(2) Estradiol propionate
   1–10 mg/week -month (intramuscular)
(3) Estradiol valerate
   5–10 mg/1–4 weeks (intramuscular)
(4) Ethinylestradiol
   0.02–0.15 mg/day (per os)
(5) Mestranol
   0.02–0.16 mg/day (per os)
(6) Estriol
   0.1–2 mg/day (per os)
   1–2 mg/week (subcutaneous, intramuscular)
(7) Estriol propionate
   5–10 mg/week—10 days (subcutaneous, intramuscular)
(8) Estriol benzoate
   5–10 mg/1–2 weeks (intramuscular)
(9) Progesterone
   10–50 mg/day (intramuscular)
(10) Estrone
   0.02–2 mg/day (per os)

II. Thyroid hormone (1) L-Thyroxine
    25–400 μg/day (per os)
(2) L-Triiodothyronine
    5–150 μg/day (per os)

Hereafter the therapeutic activity of the pharmaceutical composition according to the present invention on osteoporosis is described below.

Using model animal with severe osteoporosis caused by combination of low calcium (Ca) diet and oophorectomy, the therapeutic effect of the pharmaceutical composition according to the present invention on osteoporosis was examined.

(1) Preparation of experimental model animal with osteoporosis:

Wistar strain female rats, 7 or 8 being grouped into one, were anesthesized with ketamine hydrochloride and underwent an oophorectomy according to the usual way (OVX-low Ca control group). Rats which had a sham operation (Sham-ope low Ca group) were also used for the experiment as control.

Solid feed (Ca content, 1.23%) was used for 2 weeks after oophorectomy and low Ca powdery feed (Ca content, 0.05%) was used during administration of a test drug. In order to eliminate the inhibition of reduction in bone weight due to stimulation and physical load on the femur accompanied by increase of body weight due to oophorectomy, the animal was fed with limiting feed of 10 g/rat/day but could drink ion exchange water freely.

(2) Method for administration:

A test drug was given as a mixture with feed for 5 weeks from 2 weeks after oophorectomy. The diet composition was prepared by mixing the test drug with feed according to a mixing ratio culculated on the basis of an average feed weight for 3 days. Estradiol benzoate was administred olive oil suspension subcutaneously once a week.

After completion of the administration of the test drug, the femur was taken out and pharmacological effects of the test drug was determined by measurement of bone mineral content, soft X-ray radiography, etc.

Grouping in the pharmacological test is as follows.

Group I : Sham-ope low Ca group
Group II : OVX-low Ca control group
Group III : OVX-low Ca group administered with estradiol benzoate [dose: 1 mg/kg/week]
Group IV : OVX-low CA group administered with L-thyroxine [dose: 30 μ/kg/day]
Group V : OVX-low Ca group administered with estradiol benzoate+L-thyroxine [dose: 1 mg/kg/week+30 μ/kg/day]

(3) Pharmacological Test I

The results of the pharmacological tests are shown below.

(i) Measurement of bone mineral content:

A bone density was determined in terms of bone mineral content according to the method of Hagaman et al. [Hagaman, U.R. et al., Bone, 6, 301–305 (1985)]. The left femur was divided into 10 sections with 3.2 mm interval from the proximal end and a bone mineral content in each section was determined with a Digital Bone Densitometer.

The 10 sections was classified into 3 sites: 1 to 3 sections, 4 to 7 sections and 8 to 10 sections from the proximal end were termed a proximal femur site, a midfemur site and a distal femur site, respectively, and a bone mineral content (B.M.C.) in each site was determined.

The results are shown in Table 1.

TABLE 1

| | Bone Mineral Content (g/cm) ± S.E. | | |
|---|---|---|---|
| | Proximal femur site | Midfemur site | Distal femur site |
| Group I | 0.253 ± 0.003 | 0.206 ± 0.001 | 0.222 ± 0.001 |
| Group II | 0.227 ± 0.004 | 0.207 ± 0.002 | 0.202 ± 0.006 |
| Group III | 0.254 ± 0.004 | 0.201 ± 0.003 | 0.235 ± 0.004 |
| Group IV | 0.233 ± 0.003 | 0.206 ± 0.004 | 0.206 ± 0.007 |
| Group V | 0.270 ± 0.004 | 0.207 ± 0.003 | 0.258 ± 0.007 |

(ii) Soft X-ray radiography

A soft X-ray photograph of the left femur was taken under conditions of 40 kV/1 mA/150 secs., using an apparatus for soft X-ray photography.

In the OVX-low Ca control group, a radiograph showing reduction in bone amount was observed at the proximal and distal femur sites in which osteogenesis was to be most active, as compared to the sham-ope low Ca group.

In the group administered with the thyroid hormone, a radiograph similar to that in the OVX-low Ca control group was also obtained and any effect was not observed; in the group administered with the estrogenm, a radiograph showing a tendency to increase bone amount was observed. In the group administered with the estrogen and the thyroid hormone in combination, it was observed that a radiograph showed a more remarkable increase in bone amount than in the group administered with the estrogen alone.

As shown by the above results in measurement of bone density in terms of bone mineral content and soft X-ray radiography, the reduction in bone amount was noted especially at the proximal and distal femur sites in the OVX-low Ca control group in which ovary was removed, as compared to the Sham-ope low Ca group which underwent sham operation. It was thus recognized that animal suffered from severe osteoporosis by combination of low calcium (Ca) diet and oophorectomy.

In the present pharmacological test using the model animal with osteoporosis, an increase in bone amount was noted at the proximal and distal femur sites in the group administered with the estrogen, however, in the group administered with the thyroid hormone, an increase in bone amount was hardly observed. When the estrogen was administered in combination with the thyroid hormone, the increasing activity in bone amount was superior to the administration in the estrogen alone. For example, at the distal femur site, the bone amount was increased by 16% in the group administered with the estrogen, as compared with the OVX-low Ca control group; whereas an increase in bone amount reached 28% in the group administered with the estrogen and the thyroid hormone in combination, indicating an increase in bone amount by about 2 times that of the group administered with the estrogen alone.

(4) Pharmacological Test II

As apparently shown in the results of the Pharmacological Test I, by using the estrogen in combination with the thyroid hormone having little activity of increasing bone amount, a more excellent effect was obtained than in the case of administering the estrogen alone.

Regarding other estrogens than estradiol, the effect in combination with the thyroid hormone was investigated as the same way as the said Pharmacological Test I. In the case of actual osteoporosis, bone fracture is so often occurred in the proximal femur site, and the proximal site is predominated by cancellous bone and is a site where osteogenesis is most active. Therefore, in these investigations, the proximal site was focused and the bone mineral density (B.M.D.) was measured on that site.

The results are shown in Table 2.

TABLE 2

| | Increasing effects in bone mineral density (g/cm$^2$) as compared to the OVX-low Ca control group | |
|---|---|---|
| | estrogen alone | estrogen + L-thyroxine |
| Estrone (1 mg/kg) | 4.2% | 8.3% |
| Pregrenolone (50 mg/kg) | 3.5% | 5.5% |
| Androstendione (50 mg/kg) | 0% | 4.2% |
| Androstendiol (50 mg/kg) | 0.7% | 6.2% |
| Testosterone (50 mg/kg) | 0.7% | 3.5% |

As shown in the Table 2, by using the various kinds of estrogens in combination with the thyroid hormone, the increasing effect of the estrogen in bone amount was accelerated, and the increasing effect in bone amount was produced in the case of the estrogen having low pharmacological activity.

The epiphysis is predominated by cancellous bone and is a site where osteogenesis is most active. Since the epiphysis reflects influence of bone metabolism, it is a suitable site for evaluation of effects of a drug on model animal with osteoporosis. Therefore, as is evident from the test results described above, the pharmaceutical composition of the present invention shows a remarkable increase in bone amount at the epiphysis, which indicates excellent effects on the treatment of osteoporosis.

The composition for the treatment of osteoporosis in accordance with the present invention has been completed based on the new finding that by administering the estrogen in combination with the thyroid hormone, a more excellent activity of increasing bone amount can be obtained than in the case of administering the estrogen alone. The effect has been found and confirmed by the present invention for the first time.

Accordingly, by the pharmaceutical composition of the present invention, not only superior effects over the limit of the therapeutic effect achieved by estrogen alone heretofore can be expected but the dose of estrogen can be reduced. Thus, various side effects with which estrogen might be concerned can be alleviated. Therefore, the present invention can provide high utility.

It is further expected that the composition of the present invention would have an excellent therapeutic effect on symptoms such as climacteric difficulties, anovarism, abnormal menstruation, etc., as compared to administration of estrogen alone

EXAMPLES

The pharmaceutical composition of the present invention can be prepared into pharmaceutical preparations by using the estrogen and the thyroid hormone as the effective ingredients in combination with appropriate carriers or diluents for medical use. The composition of the invention can be prepared into pharmaceutical preparations by any ordinary ways and can be formulated into preparations forms of solid, semi-solid or liquid for oral or parenteral administration.

In formulation, the effective ingredients in the pharmaceutical composition of the present invention may be used in the form of pharmaceutically acceptable salts thereof or may also be formulated together with other pharmaceutically active components.

As preparations for oral administration, the composition may be used as it is; alternatively, the composition may also be formed into tablets, powders, granules or capsules, together with appropriate additives, for example, conventional excipients such as lactose, mannitol, corn starch, potato starch, etc., in appropriate combination with binders such as crystalline cellulose, cellulose derivatives, gum arabic, corn starch, gelatin, etc.; disintegrators such as corn starch, potato starch, CMC, etc.; lubricants such as talc, magnesium stearate, etc.; thickeners, wetting agents, buffers. preservatives, flavors, etc.

For injections, the composition may be dissolved or suspended in an aqueous solvent or in a non-aqueous solvent, for example, distilled water for injection, physiological saline, Ringer's solution, vegetable oil, synthetic fatty acid glycerides, higher fatty acid esters, propylene glycol, etc. to prepare a solution or suspension.

Furthermore, the composition of the present invention may also be kneaded with various bases, for example, oil-and-fat base such as cacao butter, emulsifiable base or water-soluble base such as Macrogol, etc., hydrophilic base, or the like to prepare a suppository.

Hereafter examples of formulation of the drug composition according to the present invention are shown but the present invention is not deemed to be limited to these examples. Formulation 1 (tablet)

| Ingredient | Per tablet (mg) |
|---|---|
| Estriol | 0.5 |
| L-Thyroxine | 0.05 |
| Corn starch | 40 |
| Magnesium stearate | 10 |
| Lactose | Proper quantity |
| Total | 250 mg |
| Formulation 2 (capsule) | |
| Ethinylestradiol | 0.02 |
| L-Triiodothyronine | 0.0125 |
| Lactose | proper quantity |
| Total | 300 mg |

While the invention has been described in detail and with reference to specific embodiments thereof, it is apparent to one skilled in the art that various changes and modifications can be made therein without departing from the spirit and the scope of the present invention.

What is claimed is:

1. A method for treatment of osteoporosis which shows an observable increase in the amount of bone, comprising administering to a host with osteoporosis an osteoporosis treating effective amount of the following components (a) and (b):
   (a) at least one first member known to have a therapeutic effect on osteoporosis selected from the group consisting of an estrogen, an estrogen precursor, a derivative thereof, an ester thereof, and a pharmacologically acceptable salt thereof, an ester thereof, and a pharmacologically acceptable salt thereof; and (b) at least one second member having a hardly observable increase in bone amount selected from the group consisting of a thyroid hormone and a pharmacologically acceptable salt thereof; whereby more increase in bone amount is obtained than is obtainable from administering component (a) along.

2. A method as claimed in claim 1, wherein said thyroid hormone is selected from the group consisting of L-thyroxine and L-triiodothyronine.

3. A method as claimed in claim 1, wherein said first member is a natural estrogen.

4. A method as claimed in claim 3, wherein said first member is an estrone.

5. A method as claimed in claim 3, wherein said first member is an estradiol.

6. A method as claimed in claim 1, wherein said first member is an estrogen precursor.

7. A method as claimed in claim 2, wherein said first member is selected from the group consisting of derivatives of natural estrogen and a natural estrogen precursor.

8. A method as claimed in claim 1, wherein said first member is selected from the group consisting of estrone, estradiol, estriol, ethinylestradiol, mestranol, estrone sulfate sodium salt, equilin sulfate sodium salt and prasterone sulfate sodium salt.

* * * * *